US Patent [19]
Kato et al.

[11] Patent Number: 4,874,890
[45] Date of Patent: Oct. 17, 1989

[54] PROCESS FOR THE PRODUCTION OF DEUTERATED METHYL ACRYLATE OR DEUTERATED METHYL METHACRYLATE

[75] Inventors: Masaaki Kato; Tetsuya Uno; Masao Kobayashi; Naoto Osuga, all of Otake, Japan

[73] Assignee: Mitsubishi Rayon Co., Ltd., Tokyo, Japan

[21] Appl. No.: 154,485

[22] Filed: Feb. 8, 1988

Related U.S. Application Data

[63] Continuation of Ser. No. 807,710, Dec. 11, 1985, abandoned.

[30] Foreign Application Priority Data

Dec. 21, 1984 [JP] Japan ................................ 59-270319

[51] Int. Cl.$^4$ ............................................. C07C 69/52
[52] U.S. Cl. .................................................... 560/205
[58] Field of Search ......................................... 560/205

[56] References Cited

PUBLICATIONS

Atkinson, Joseph G. et al. *Chemical Abstracts* (1972) #156,509e.
Lockley, William J. S. *Synth. Appl. Isot. Labeled Compd. Proc. Int. Symp.* (*1982*) Publ. 1983.
Lockley, William J. S. Chemical Abstracts vol. 98 (1983) #215,266a.

*Primary Examiner*—Paul J. Killos
*Attorney, Agent, or Firm*—Armstrong, Nikaido, Marmelstein, Kubovcik & Murray

[57] ABSTRACT

There is provided the improved process for the production of deutrated methyl acrylate or methacrylate by the direct substitution of deuterium for hydrogens in methyl acrylate or methacrylate in the presence of a platinum Group metal catalyst.

10 Claims, No Drawings

PROCESS FOR THE PRODUCTION OF DEUTERATED METHYL ACRYLATE OR DEUTERATED METHYL METHACRYLATE

This application is a continuation of application Ser. No. 807,710, filed Dec. 11, 1985.

FIELD OF THE INVENTION

This invention relates to a process for the production of deuterated methyl acrylate or deuterated methyl methacrylate.

DESCRIPTION OF THE PRIOR ART

Prior art methods for the production of deuterated methyl methacrylate include a production process via deuterated acetone cyanhydrin proposed in the Journal of Polymer Science 62, S95 (1962). This consists of preparing deuterated acetone cyanhydrin from deuterated acetone and hydrocyanic acid, treating this with sulfuric acid to form the sulfate of methacrylamide, then reacting this sulfate with deuterated methanol to give deuterated methyl methacrylate.

DETAILED DESCRIPTION OF THE INVENTION

However, in prior art methods of preparation, the use of deuterated starting materials such as deuterated acetone and deuterated methanol has proven economically unsatisfactory because of the large number of reaction steps involved. For this reason, an improved method involving fewer steps has been sought. After extensive research on efficient and practical methods for the production of deuterated methyl methacrylate, we discovered a novel manufacturing process involving the direct substitution of the hydrogens in methyl methacrylate with deuterium, which led us ultimately to the present invention.

Now, it has been found that the preferred order of substitution of methyl methacrylate hydrogens by deuterium is (a), (b), (c), then (d), these positions of hydrogens to be substituted being as follows:

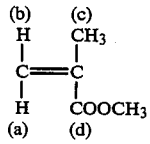

The comparative ease of deuterium substitution at these positions is as follows:

olefinic hydrogen (a, b) > α-methyl hydrogen (c) > methyl hydrogen (ester group) (d)

For example, in the case of a total deuteration ratio of about 33%, the deuteration ratio at each position is approximately as follows:

a = about 52%
b = ' 52%
c = ' 52%
d = very small

According to the present invention, there is provided a process for the manufacture of deuterated methyl acrylate or deuterated methyl methacrylate comprising the direct substitution of deuterium for hydrogen within methyl acrylate or methyl methacrylate in the presence of a catalyst.

The hydrogen-deuterium substitution of methyl acrylate or methyl methacrylate, according to the present invention is carried out in the presence of a catalyst and at from room temperature to 300° C., but a temperature from 50 to 150° C. is preferable from the standpoint of reaction rate as well as the inhibition of side reactions and polymerization.

As the deuterium source heavy water or heavy water and deuterium gas may be employed, and at least a stoichiometric amount of deuterium with respect to the methyl acrylate or methyl methacrylate must be present within the reaction system.

Referring to the catalyst, element(s) selected from the platinum group metals of the Periodical Table or compounds thereof are catalytically effective. Platinum, palladium, or compounds thereof are especially preferably. Where necessary, the catalyst may be supported on a suitable carrier such as alumina, silica, silicaalumina, diatomaceous earth, active carbon, or the like.

The reaction may be conducted either in a gaseous phase or a liquid phase, and where suitable, under the application of pressure. To inhibit polymerization during the reaction, a polymerization inhibitor such as phenothiazine, hydroquinone or the like may be added as required. Polymerization may also be inhibited by allowing a small amount of oxygen to be present in the reaction mixture.

This direct deuteration has a number of technical and economic advantages over prior art processes. In syntheses by the conventional acetone cyanhydrin (AcH) process, use is made of deuterated methanol and deuterated acetone in place of methanol and acetone. Deuterated acetone is prepared by direct substitution between heavy water and acetone, while deuterated methanol is synthesized by first preparing deuterium from heavy water, then combining the deuterium with carbon monoxide. Both are costly products because of being normally used as reagents. By contrast, in the synthesis of deuterated methyl methacrylate (d-MMA) by direct substitution, the fact that the only starting material required for deuteration is heavy water greatly cuts costs. Moreover, the sheer simplicity of this process has a very significant effect on the overall economics of the production process.

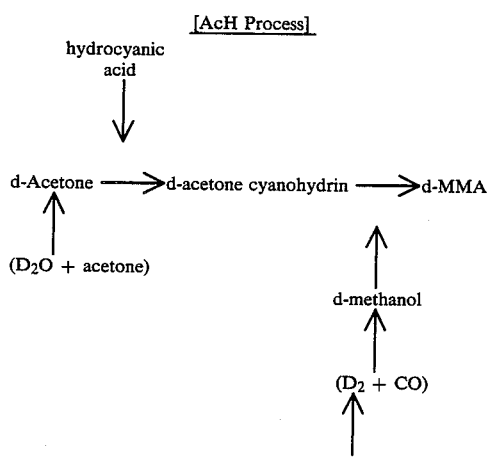

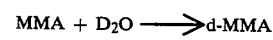

MMA + D$_2$O ⟶ d-MMA

Deuterated methyl methacrylate and deuterated methyl acrylate are used as materials in the manufacture of optical fibers. Their use permits a major improvement in the ability to transmit light, compared with undeuterated methyl methacrylate and methyl acrylate. At the light transmission wavelength, undeuterated fiber is strongly affected by the vibration absorption of the C—H bonds. Converting the C—H bonds to C—D bonds by deuteration removes the influence of C—H vibration absorption, thereby improving the ability of the fiber to transmit light. Completely deuterated material provides the best results, but even partial deuteration is effective to a certain degree.

In working the process of the invention, a solvent such as dimethyl formamide that is stable at the temperature of the reaction may be used where necessary.

PREFERRED EMBODIMENTS OF THE INVENTION

The objects and advantages of the present invention shall become clearer from the following embodiments, which more concretely illustrate the invention but in no way restrict its scope. All references to "parts" signify parts by weight. Analyses were conducted by means of a gas chromatograph and a mass spectrometer. The deuteration ratio is defined as follows:

$$\text{Deuteration ratio} = \frac{\text{Number of deuterium atoms in deuterated methyl acrylate or deuterated methyl methacrylate product}}{\text{Number of hydrogen atoms in methyl acrylate or methyl methacrylate starting material}} \times 100$$

EXAMPLE 1

Ten parts of methyl methacrylate, 48 parts of heavy water, 0.5 part of potassium chloroplatinate, and a small quantity of hydroquinone as the polymerization inhibitor were placed in a small reactor and reacted for 16 hours at 120° C. under stirring. After cooling, the reaction product was analyzed and found to be deuterated methyl methacrylate with a deuteration ratio of 58%.

EXAMPLE 2

The same process was carried out as in Example 1, except that the ten parts of methyl methacrylate was replaced with 8,6 parts of methyl acrylate, and the reaction temperature was changed from 120° C. to 90° C. This gave deuterated methyl acrylate with a deuteration ratio of 42%.

EXAMPLE 3

Twenty-five parts of methyl methacrylate, 40 parts of heavy water, 1.0 part of chloroplatinic acid, and a small quantity of hydroquinone as the polymerization inhibitor were placed in a 100 ml flask fitted with a condenser and reacted for 65 hours at 85° C. under stirring. This gave deuterated methyl methacrylate with a deutration ratio of 41%.

EXAMPLES 4–6

These reactions were carried out as in Example 1 except that the 0.5 part of potassium chloroplatinate was replaced with 3.4 parts of rhodium chloride, 10 parts of 1% palladium catalyst supported on active carbon, or 0.5 part of dichlorotris(triphenylphosphine)ruthenium, and the reaction temperature and time were changed as shown in Table 1. The results are given in Table 1.

TABLE 1

| Example | Catalyst | Reaction Temp. (°C.) | Time (hrs.) | Deuteration Ratio (%) |
|---|---|---|---|---|
| 4 | rhodium chloride | 100 | 40 | 45 |
| 5 | Pd-active carbon | 90 | 62 | 30 |
| 6 | dichloro-tris-(triphenylphosphine)ruthenium | 95 | 24 | 15 |

We claim:

1. A process for the production of deuterated methyl acrylate or deuterated methyl methacrylate, comprising the direct substitution of deuterium, from a source chosen from at least one of heavy water and deuterium gas, for the hydrogens in methyl acrylate or methyl methacrylate in the presence of at least one platinum group metal catalyst selected from the group consisting of platinum and palladium catalysts at a temperature in the range of from room temperature up to 300° C.

2. A process according to claim 1, wherein said catalyst is a platinum catalyst.

3. A process according to claim 2, wherein said catalyst is elemental platinum.

4. A process according to claim 2, wherein said catalyst is a platinum compound.

5. A process according to claim 2, wherein said temperature is between 50° C. and 150° C.

6. A process according to claim 1, wherein said temperature is between 50° C. and 150° C.

7. A process according to claim 1, wherein said catalyst is a palladium catalyst.

8. A process according to claim 7, wherein said catalyst is elemental palladium.

9. A process according to claim 7, wherein said catalyst is a palladium compound.

10. A process according to claim 7, wherein said temperature is between 50° C. and 150° C.

* * * * *